(12) United States Patent
Campitelli et al.

(10) Patent No.: US 12,053,019 B2
(45) Date of Patent: Aug. 6, 2024

(54) PIERCING DEVICE FOR INHALER ARTICLE

(71) Applicant: PHILIP MORRIS PRODUCTS S.A., Neuchâtel (CH)

(72) Inventors: Gennaro Campitelli, Bologna (IT); Onur Dayioglu, Neuchâtel (CH); Fabiana Spadaro, Neuchâtel (CH); Gérard Zuber, Neuchâtel (CH)

(73) Assignee: Philip Morris Products S.A., Neuchâtel (CH)

( * ) Notice: Subject to any disclaimer, the term of this patent is extended or adjusted under 35 U.S.C. 154(b) by 217 days.

(21) Appl. No.: 17/435,133

(22) PCT Filed: Mar. 2, 2020

(86) PCT No.: PCT/IB2020/051761
§ 371 (c)(1),
(2) Date: Aug. 31, 2021

(87) PCT Pub. No.: WO2020/178715
PCT Pub. Date: Sep. 10, 2020

(65) Prior Publication Data
US 2022/0132917 A1    May 5, 2022

(30) Foreign Application Priority Data
Mar. 5, 2019    (EP) .................................. 19160888

(51) Int. Cl.
*A24F 13/08* (2006.01)
*A24F 42/20* (2020.01)
*A24F 42/60* (2020.01)

(52) U.S. Cl.
CPC .............. *A24F 13/08* (2013.01); *A24F 42/20* (2020.01); *A24F 42/60* (2020.01)

(58) Field of Classification Search
CPC ........... A24F 13/08; A24F 42/20; A24F 42/60
See application file for complete search history.

(56) References Cited

U.S. PATENT DOCUMENTS 5,476,093 A * 12/1995 Lankinen .......... A61M 15/0028
128/203.15
5,501,236 A * 3/1996 Hill ........................ A24F 42/20
131/273
(Continued)

FOREIGN PATENT DOCUMENTS

WO    1991/018636    12/1991
WO    2015/0166350    11/2015
(Continued)

OTHER PUBLICATIONS

International Preliminary Report on Patentability for PCT/IB2020/051761, issued Sep. 16, 2021; 7 pages.
(Continued)

*Primary Examiner* — Christopher M Rodd
*Assistant Examiner* — Jennifer A Kessie
(74) *Attorney, Agent, or Firm* — Mueting Raasch Group

(57) ABSTRACT

A piercing device (150) contains a recessed piercing element (160) and is configured to receive a distal end (118) of an inhaler article (110). The piercing element pierces or punctures a single hole into a capsule contained within the inhaler article when the inhaler article is seated into an inhaler article cavity (157) of the piercing device. The piercing device includes a marking element (170) extending into the inhaler article cavity from the housing inner surface (152). The marking element is configured to mark an outer surface of an inhaler device when the inhaler device is received within the inhaler article cavity. The marking element extends orthogonally to the piercing element longitudinal axis.

14 Claims, 3 Drawing Sheets

(56) References Cited

Figure 1:
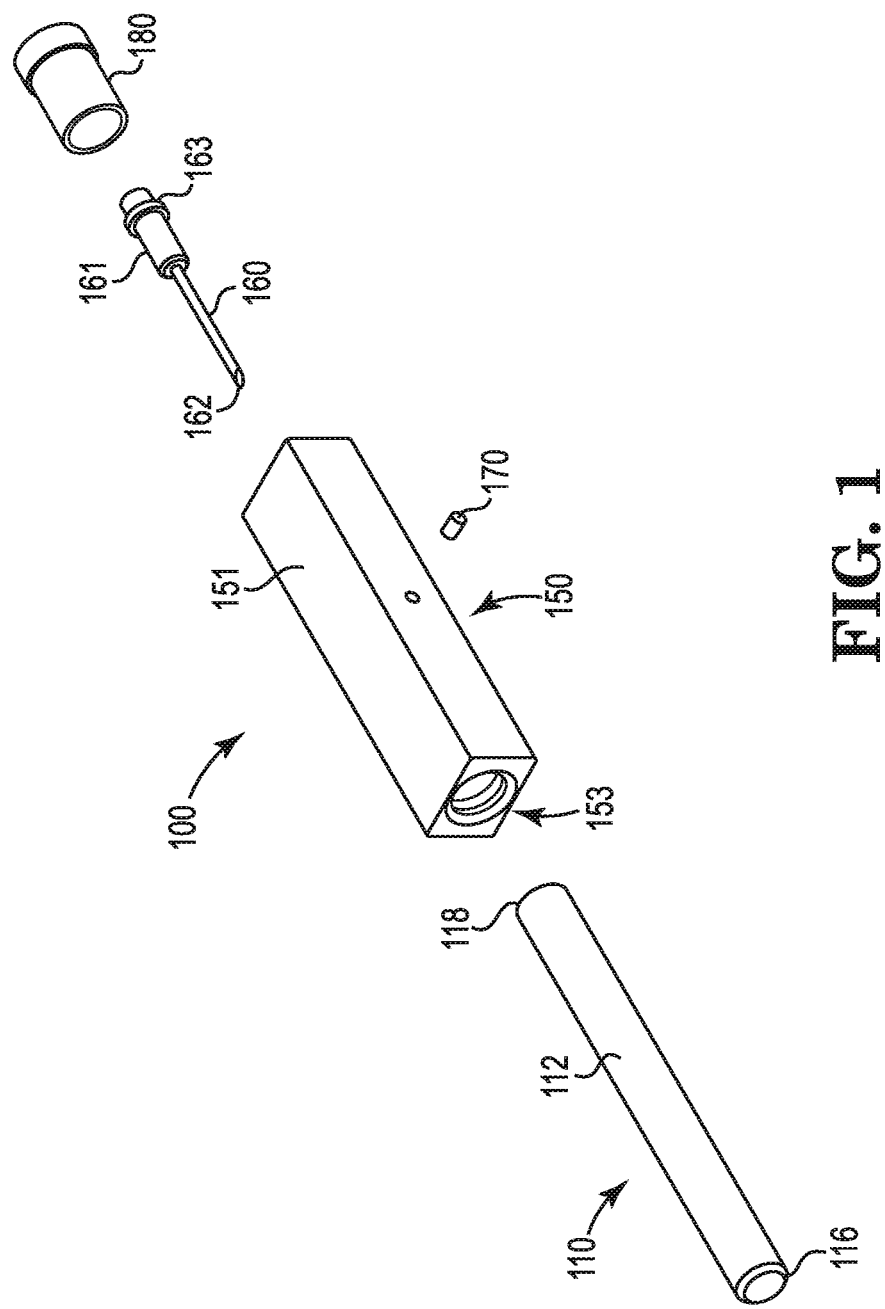

U.S. PATENT DOCUMENTS 9,700,076 B2 7/2017 Xiang
2017/0196262 A1* 7/2017 Brereton ................. A24F 42/60

FOREIGN PATENT DOCUMENTS

WO   WO-2017068095 A1 *   4/2017   ........... A24B 15/167
WO   2017/109626          6/2017
WO   2018/007886          1/2018

OTHER PUBLICATIONS

European Search Report for EP 19160888.4, issued by the European Patent Office; 7 pgs.
International Search Report and Written Opinion for PCT/IB2020/051761, issued by the European Patent Office, 14 pgs.

\* cited by examiner

PIERCING DEVICE FOR INHALER ARTICLE

This application is the § 371 U.S. National Stage of International Application No. PCT/IB2020/051761, filed 2 Mar. 2020, which claims the benefit of European Application No. 19160888.4, filed 5 Mar. 2019, the disclosures of which are incorporated by reference herein in their entireties.

This disclosure relates to a piercing device for an inhaler article and inhaler systems that include the piercing device and inhaler article. The piercing device is configured to mark the inhaler article to indicate that the inhaler article has been activated.

Dry powder inhalers are not always fully suitable to provide dry powder particles to the lungs at inhalation or air flow rates that are within conventional smoking regime inhalation or air flow rates. Dry powder inhalers may be complex to operate or may involve moving parts. Dry powder inhalers often strive to provide an entire dry powder dose or capsule load in a single breath.

It would be desirable to provide an inhaler system that minimizes moving parts. It would be desirable that this piercing device have a protected piercing end. It would be desirable to provide an inhaler system with a reusable piercing device. It would be desirable to provide an inhaler system that includes a low-profile and reusable piercing device. It would be desirable to provide an inhaler system that provided a visual indication that the inhaler article has been activated.

This disclosure is directed to a piercing device for an inhaler article. The piercing device and inhaler article may form an inhaler system.

The piercing device includes a recessed piercing element and a marking element. The piercing element pierces or punctures a hole into a capsule contained within an inhaler article when the inhaler article is seated into an inhaler article cavity of the piercing device. The marking element extends into the inhaler article cavity from the housing inner surface. The marking element is configured to mark an outer surface of an inhaler device when the inhaler device is received within the inhaler article cavity.

The piercing element pierces or punctures a single hole into the capsule contained within the inhaler article when the inhaler article is seated into the piercing device. The piercing element includes a marking element that is configured to mark the inhaler article with an indicator that the inhaler article has been activated. The inhaler article is separated from the piercing device and then utilized by a consumer. The piercing device may be re-utilized on subsequent inhaler articles.

A piercing device includes a housing, having a housing outer surface and a housing inner surface. The housing inner surface defines an inhaler article cavity. The housing extends along a housing longitudinal axis from a distal end to an open proximal end a housing length. The housing open proximal end is configured to receive the distal end of an inhaler article into the inhaler article cavity. A piercing element is fixed to and extends from the housing inner surface into the inhaler article cavity along a piercing element longitudinal axis a piercing element length. The piercing element is recessed from the open proximal end a recessed distance. A marking element extends into the inhaler article cavity from the housing inner surface. The marking element is configured to mark the surface of an inhaler article when the inhaler article is received within the inhaler article cavity.

A piercing device includes a housing, having a housing outer surface and a housing inner surface. The housing inner surface defines an inhaler article cavity. The housing extends along a housing longitudinal axis from a distal end to an open proximal end a housing length. The housing open proximal end is configured to receive the distal end of an inhaler article into the inhaler article cavity. A piercing element is fixed to and extends from the housing inner surface into the inhaler article cavity along a piercing element longitudinal axis a piercing element length. The piercing element is recessed from the open proximal end a recessed distance. A marking element extends into the inhaler article cavity from the housing inner surface. The marking element is configured to mark the surface of an inhaler article when the inhaler article is received within the inhaler article cavity. The marking element extends orthogonally to the piercing element longitudinal axis.

Advantageously, the inhaler system provides an inhaler system that minimizes moving parts. Advantageously, the inhaler system utilizes a separate piercing device. This may enable the piercing device to be reusable and the inhaler article to be disposable after a single use. Advantageously, the piercing element is removably coupled to the body of the piecing device so that it may be easily replaced. Advantageously, the inhaler system provides nicotine particles to the lungs at inhalation or air flow rates that are within conventional smoking regime inhalation or air flow rates. The inhaler article delivers the nicotine powder with an inhaler article that has a form similar to a conventional cigarette. The piercing device may be formed using a simple manufacturing method.

The marking element may extend orthogonally to the piercing element longitudinal axis. The marking element may be configured to mark the outer surface of an inhaler article in a mechanical manner. For example, the marking element may be configured to scratch, cut, abrade, score, fold, or bend the outer surface of the inhaler article. The marking element may have a sharp end configured to scratch the inhaler outer surface when received within the inhaler article cavity. The marking element may apply a color to the inhaler outer surface when received within the inhaler article cavity. The marking element may mark the inhaler outer surface when the piercing element penetrates a capsule disposed within the inhaler article.

The marking element may mark the outer surface of an inhaler article as the inhaler article is inserted into the inhaler article cavity. The marking element may mark the outer surface of an inhaler article as the inhaler article is removed from the inhaler article cavity. The marking element may mark the outer surface of an inhaler article as the inhaler article is both inserted into, and removed from the inhaler article cavity.

The mark applied to the outer surface of outer surface of an inhaler article by the marking element may have any shape. The mark applied to the outer surface of outer surface of an inhaler article by the marking element may be a line generally extending in the longitudinal direction of the inhaler article longitudinal axis. The line may have any length.

Advantageously, the piercing device includes a marking element configured to mark the inhaler article to indicate that the inhaler article has been activated. The mark or indication may provide a visual indication that the inhaler article has been activated.

The piercing element may be recessed from the open proximal end a recessed distance of at least about 25% of the housing length. The piecing device housing may have a tapered inner diameter that decreases from the open end to the recessed end. The housing inner diameter may taper down in a range from about 3% to about 13%, or in a range from about 5% to about 10%.

Advantageously, recessing the protected piercing element may facilitate protection of the piercing element and protection for a user from the piercing element. Advantageously, the tapered inner diameter may provide a guided alignment of the piercing element to accurately puncture the capsule within the inhaler article. The tapered inner diameter may provide a reliable hard stop or interference fit with the outer surface of the inhaler article when the inhaler article is fully seated or received within the piecing device. Tapering the inner diameter of the cylindrical housing may facilitate locating the piercing device on the distal end of the inhaler article.

The inhaler article cavity may have a closed distal end and the piercing element may extend through the closed distal end. The distal end of the housing may define a piercing element cavity where the closed distal end defines the base of the piercing element cavity and the piercing element cavity receives the piercing element. The inhaler article may further include a retaining element configured to retain the piercing element within the piercing element cavity. The retaining element may form a portion of the distal end of the housing and the retaining element may be removably coupled to the housing.

Advantageously, the piercing element may be removably coupled to the body of the piecing device so that it may be easily replaced.

The inhaler system described herein may provide a dry powder to the lungs at inhalation or air flow rates that are within conventional smoking regime inhalation or air flow rates. A consumer may take a plurality of inhalations or "puffs" where each "puff" delivers a fractional amount of dry powder contained within a capsule contained within the capsule cavity. This inhaler article may have a form similar to a conventional cigarette and may mimic the ritual of conventional smoking. This inhaler article may be simple to manufacture and convenient to use by a consumer.

Air flow management through a capsule cavity of the inhaler article may cause a capsule contained therein to rotate during inhalation and consumption. The capsule may contain particles containing nicotine (also referred to as "nicotine powder" or "nicotine particles") and optionally particles comprising flavour (also referred to as "flavour particles"). Rotation of the pierced capsule may suspend and aerosolize the nicotine particles released from the pierced capsule into the inhalation air moving through the inhaler article. The flavour particles may be larger than the nicotine particles and may assist in transporting the nicotine particles into the lungs of the user while the flavour particles preferentially remain in the mouth or buccal cavity of the user. The nicotine particles and optional flavor particles may be delivered with the inhaler article at inhalation or air flow rates that are within conventional smoking regime inhalation or air flow rates.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof.

The terms "proximal" and "distal" are used to describe the relative positions of components, or portions of components, of the piercing device, inhaler article, or system. Piercing devices or elements (such as the sleeve) forming the piercing device, according to the invention have a proximal end which, in use, receives an inhaler article and an opposing distal end which may be a closed end, or have an end closer to the proximal end of the piercing device. Inhaler articles, according to the invention have a proximal end which, in use, particles exit the inhaler article for delivery to a user and have an opposing distal end. The proximal end of the inhaler article may also be referred to as the mouth end.

The piercing device described herein may be combined with an inhaler article containing a capsule for activating the inhaler article by piercing the capsule, providing an indication that the capsule has been activated on the surface of the inhaler article, and releasing the particles contained inside the capsule and enabling the article to deliver the particles to a consumer. The piercing device is separate from the inhaler article. A plurality of these inhaler articles may be combined with a piercing device to form a kit. A single piercing element may be utilized on 10 or more, or 25 or more, or 50 or more, or 100 or more, inhaler articles to activate (puncture or pierce) a capsule contained within each inhaler article and provide a visual indication (marking) on each inhaler article of the activation of the inhaler article.

An inhaler article includes a body extending along a longitudinal axis from a mouthpiece end to a distal end. The body has an inhaler length extending between the mouthpiece end and the distal end. The body defines an inhaler outer surface. A capsule cavity is defined within the body and extends along the longitudinal axis. A mouthpiece air channel extends from the capsule cavity to the mouthpiece end. A boundary element is between the capsule cavity and the mouthpiece air channel. The boundary element includes apertures fluidly connecting the capsule cavity with the mouthpiece air channel. The distal end may include an end cap or endpiece element.

The piercing device includes a housing. The housing defines a housing outer surface and a housing inner surface. The housing inner surface defines an inhaler article cavity. The housing inner surface may define a cylindrical cavity. The housing extends along a housing longitudinal axis from a distal end to an open proximal end, a housing length. The housing open proximal end is configured to receive the distal end of the inhaler article into the inhaler article cavity.

A piercing element is contained within and fixed to the housing inner surface. The piercing element extends along a piercing element longitudinal axis from a fixed distal end to a piercing end a piercing element length. The piercing element is recessed from the open proximal end a recessed distance.

A marking element extends into the inhaler article cavity from the housing inner surface. The marking element is configured to mark the inhaler outer surface when received within the inhaler article cavity. The marking element may be configured to mark the inhaler outer surface only when the piercing element penetrates a capsule received within the inhaler article, thus indicating that the inhaler articles has been activated and may be consumed by a user. This may also advantageously prevent a user trying to reuse an inhaler article which has already been used.

The marking element may extend orthogonally to the piercing element longitudinal axis. The marking element may be formed of a rigid material configured to provide a visual indication that the marking element has contacted the inhaler outer surface. The marking element may be fixed to the piercing device housing.

The marking element may extend though at least a portion of a thickness of the piercing device housing. The marking element may extend beyond the at least the housing inner surface and into the inhaler article cavity. The marking element may extend beyond the at least the housing inner surface a marking distance so that the marking element contacts the inhaler outer surface when the inhaler article is received within the inhaler article cavity.

The marking element may define a pin shape having a length greater than its diameter. The marking element may be threaded and resemble a screw. The distance the marking element extends into the inhaler article receptacle may be varied by the consumer. For example, the marking element may be rotated to change the distance the marking element extends into the inhaler article receptacle. This may advantageously allow the marking element to be used with different inhaler articles having different diameters. The marking element may have a length that is greater than the thickness of the piercing article housing that it extends through.

The marking element may have a sharp end configured to scratch the inhaler outer surface when received within the inhaler article cavity. This marking element may be formed from a metal. This sharp marking element may form a scratch that is visually apparent to the consumer. The visual scratch on the inhaler outer surface may indicate that the piercing element penetrated a capsule received within the inhaler article, thus indicating that the inhaler article has been activated and may be consumed by a user.

The marking element may apply a color to the inhaler outer surface when received within the inhaler article cavity. The marking element may include at least one of, a graphite core, chalk, and ink to provide a visual color mark that is apparent to the consumer. The visual color mark on the inhaler outer surface may indicate that the piercing element penetrated a capsule received within the inhaler article, thus indicating that the inhaler article has been activated and may be consumed by a user.

Recessing the piercing element into the housing protects the piercing element from coming into contact with surfaces not intended to be received within the piercing element. Recessing the piercing element into the housing may also protect the piercing element from being damaged or modified by surfaces not intended to be received within the piercing element.

The piercing element may be recessed from the open proximal end by any suitable recessed distance. For example, the piercing element may be recessed from the open proximal end a recessed distance of at least about 10%, at least about 20%, at least about 25%, or at least about 30%, or at least about 35%, or at least about 40%, of the housing length. The piercing element may be recessed from the open proximal end a recessed distance of in a range from about 5% to about 50%, or from about 10% to about 40%, or from about 15% to about 40%, or about 20% to about 40%, of the housing length.

The piercing element length may be any suitable length relative to the housing length. For example, the piercing element length may be about 25% to about 60%, or about 30% to about 50%, of the housing length. A distal end of the piercing element may be fixed to the distal end adjacent to or at the distal end of the housing. The piercing element entire length may be coextensive within the housing length.

The housing inner surface has an open proximal end diameter and a distal end diameter. The distal end diameter may be less than the open proximal end diameter. The housing inner surface diameter may taper down from the open proximal end diameter to the distal end diameter. The housing inner surface diameter may taper down by any suitable amount. For example, the housing inner surface diameter may taper down in a range from about 3% to about 13%, or about 5% to about 10% of the housing inner diameter at the proximal end.

The piercing element is formed of a rigid material. The rigid material is sufficiently rigid to pierce, puncture or activate a capsule contained within the inhaler article. The piercing element may be formed of a metal. The piercing element may be formed of stainless steel, such as 316 stainless steel, for example. The piercing element may be formed of a polymeric material. The piercing element may be formed of a fibre-reinforced polymeric material.

Polymeric materials useful for forming the piercing element include polycarbonate, polypropylene, polyethylene, nylon, acrylonitrile butadiene styrene, styrene acrylonitrile, polyacrylate, polystyrene, PBT polyester, PET polyester, polyoxymethylene, polysulfone, polyethersulfone, polyethereetherketone, or liquid crystal polymer, for example. Polycarbonate or liquid crystal polymer are preferred materials for forming the piercing element.

The polymeric material may be fibre-reinforced and include a plurality of fibres forming a fibre dispersion throughout the piercing element. Fibres forming this fibre dispersion may have an average length of less than about 1 mm, or in a range from about 0.1 mm to about 1 mm, and an average diameter of less than 50 micrometers. The fibres forming the fibre dispersion may be formed of glass, carbon, basalt, graphite, DuPont Kevlar brand aramid fibres, ceramics, natural fibres, polymeric fibres, and metal, for example. Preferably fibres forming the fibre dispersion are composed of glass fibres. The fibre dispersion when present in the polymeric material forming the piercing element may range from about 5% to about 60% by weight, or from about 10% to about 50% by weight, or from about 20% to about 45% by weight, or from about 30% to about 40% by weight. Fibre-reinforced polycarbonate or fibre-reinforced liquid crystal polymer are preferred materials for forming the piercing element.

The housing may be formed of any rigid material. The housing may be formed of a polymeric material. Polymeric materials useful for forming the housing include polycarbonate, polypropylene, polyethylene, nylon, acrylonitrile butadiene styrene, styrene acrylonitrile, polyacrylate, polystyrene, PBT polyester, PET polyester, polyoxymethylene, polysulfone, polyethersulfone, polyethereetherketone, or liquid crystal polymer, for example. Polyproplyene, polyethylene or co-polymers thereof are preferred materials for forming the housing.

The polymeric material forming the housing may be a different type of polymeric material than the polymeric material forming the piercing element. In one example, the polymeric material forming the housing may be polyproplyene, polyethylene or co-polymers thereof, and the polymeric material forming the piercing element may be fibre-reinforced polycarbonate, liquid crystal polymer, or fibre-reinforced liquid crystal polymer.

The piercing element may define two or more diameters. The piercing element may have a first diameter adjacent the piercing end and a second diameter being greater than the first diameter adjacent to the fixed distal end. The piercing element may have a first length segment adjacent the piercing end and a second length segment adjacent to the fixed distal end. The first length segment may have a substantially constant or uniform diameter. The second length segment may have a substantially constant or uniform diameter, or the second length segment may have a tapering diameter decreasing from the fixed distal end to the first length segment.

The inhaler article may be received into the piercing device such that the inhaler article outer surface and the piercing device housing outer surface are concentric. The piercing element longitudinal axis may be coaxial with the housing longitudinal axis, and the inhaler longitudinal axis, when the inhaler article is received within the piercing device. At least about 50%, or at least about 75% of the housing length may be coextensive with the inhaler length, when the inhaler article is received within the piercing device.

The piercing device may be formed by insertion moulding techniques. The piercing element may first be formed by moulding, for example, and then the housing may be moulded around the piercing element bonding to the piercing element. The piercing element may be a metal piercing element, the housing may be moulded around the metal piercing element fixing the metal piercing element to the housing. A metal piercing element may include protrusions or recesses at the distal end of the piercing element to increase surface area of the distal end of the piercing element and improve fixation within the housing moulded material.

The piercing element may be removable and replaceable within the piercing article. The inhaler article cavity may have a closed distal end and the piercing element may extends through the closed distal end. The closed distal end may have an aperture sized to receive and allow the piercing element to extend through the aperture.

The closed distal end may define a base of a piercing element cavity defined at the distal end of the housing. The piercing element cavity may receive the piercing element. In these embodiments, the piercing element may include a collar to fix the piercing element within the piercing element cavity. A retaining element may be configured to retain the piercing element within the piercing element cavity. The retaining element may form a portion of the distal end of the housing and the retaining element may be removably coupled to the housing. The retaining element may be reliably removed from the distal end of the housing to replace the piercing element. Once the piercing element is replaced into the piercing element cavity, the retaining element may be replaced to maintain the piercing element in the piercing element cavity.

An inhaler article air channel may extend through the end cap or endpiece element of the inhaler article to provide airflow through the inhaler article. The air channel supplying airflow to the capsule cavity may be configured to induce a swirling air flow pattern within the capsule cavity of the inhaler body. The air channel configuration may induce rotational air flow or swirling air flow as the air flows through the air channel and through the capsule cavity. Air flow through the inhaler device may enter the inhaler device at the distal end of the inhaler device and moves along the longitudinal axis of the inhaler device to the mouthpiece end. Air flow through the inhaler device may enter the inhaler device along the inhaler body upstream or along the capsule cavity and move along the longitudinal axis of the inhaler device to the mouthpiece end.

The inhaler article end cap or endpiece element may include a linear piercing channel extending through the length of the end cap or end piece element. The linear piercing channel may extend along a central axis of the end cap or end piece element. The linear piercing channel may be co-axial with the longitudinal axis of the inhaler body. The linear piercing channel may be sized to allow a piercing element to pass through the linear piercing channel. The end cap or endpiece element may define a resealable element disposed along or within the linear piercing channel. The resealable element may seal the linear piercing channel. The resealable element may form an airtight seal or barrier along the linear piercing channel, when a piercing element is not within the resealable element. The linear piercing channel may be formed of a pierce-able material. A piercing element may pass through the resealable element and puncture the capsule within the capsule cavity. The resealable element may reseal once the piercing element is retracted or removed from the resealable element. Resealable elements or membranes may include a septum or septum-like element. Resealable elements or membranes may be formed of elastic material such as rubber, silicone, metal foil co-laminated with a polymer, or latex and the like, or cellulose acetate tow, such as high-density cellulose acetate tow.

The inhaler body may resemble a smoking article or cigarette in size and shape. The inhaler body may have an elongated body extending along the longitudinal axis of the inhaler article. The inhaler body may have a substantially uniform outer diameter along the length of the elongated body. The inhaler body may have a circular cross-section that may be uniform along the length of the elongated body. The inhaler body may have an outer diameter in a range from about 6 mm to about 10 mm, or from about 7 mm to about 10 mm, or about 7 mm to about 9 mm, or about 7 mm to about 8 mm or about 8 mm. The inhaler body may have a length (along the longitudinal axis) in a range from about 40 mm to about 90 mm, or from about 50 mm to about 80 mm, or about 50 mm to about 70 mm, or 55 mm.

The capsule cavity may define a cylindrical space configured to contain a capsule (that may have an obround shape or a circular cross-section, for example). The capsule cavity may have a substantially uniform or uniform diameter along the length of the capsule cavity. The capsule cavity may have a fixed cavity length. The capsule cavity has a cavity inner diameter, orthogonal to the longitudinal axis, and the capsule has a capsule outer diameter. The capsule cavity may be sized to contain an obround capsule. The capsule cavity may have a substantially cylindrical or cylindrical cross-section along the length of the capsule cavity. The capsule cavity may have a uniform inner diameter. The capsule may have an outer diameter that is about 85% to about 95% of the inner diameter of the capsule cavity. The configuration of the capsule cavity relative to the capsule may promote limited movement of the capsule during activation or piercing of the capsule.

The configuration of the capsule cavity relative to the capsule may promote the capsule to rotate with stability within the capsule cavity. The longitudinal axis of the capsule may rotate with stability co-axially with the longitudinal axis of the inhaler body during inhalation.

Stable rotation refers to the longitudinal axis of the inhaler body being substantially parallel or co-axial with the axis of rotation of the capsule. Stable rotation may refer to the absence of procession of the rotating capsule. Preferably the longitudinal axis of the inhaler body may be substantially coextensive with the axis of rotation of the capsule. Stable rotation of the capsule may provide a uniform entrainment of a portion of nicotine particles from the capsule over two or more, or five or more, or ten or more "puffs" or inhalations by a consumer.

The capsule may be sealed within the inhaler article prior to consumption. The inhaler article may be contained within a sealed or airtight container or bag. The inhaler article may include one or more peelable or removable seal layers to cover the one or more air inlet channels or the air outlet or mouthpiece of the inhaler article.

The capsule may rotate about its longitudinal or central axis when air flows through the inhaler article. The capsule may be formed of an airtight material that may be pierced or punctured by a piercing element that may be separate or combined with the inhaler. The capsule may formed of a metallic or polymeric material that serves to keep contaminates out of the capsule but may be pierced or punctured by a piercing element prior to consumption of the nicotine particles within the capsule. The capsule may be formed of a polymer material. The polymer material may be hydroxypropylmethylcellulose (HPMC). The capsule may be a size 1 to size 4 capsule, or a size 3 capsule.

The separate piercing device, described, forms a single aperture through the capsule received in the capsule cavity. The piercing device piercing element may pass through the resealable element sealing the piercing channel on the end cap.

The capsule contains nicotine particles comprising nicotine (also referred to as "nicotine powder" or "nicotine particles") and optionally particles comprising flavour (also referred to as "flavour particles). The capsule may contain a predetermined amount of nicotine particles and optional flavour particles. The capsule may contain enough nicotine particles to provide at least 2 inhalations or "puffs", or at least about 5 inhalations or "puffs", or at least about 10 inhalations or "puffs". The capsule may contain enough nicotine particles to provide from about 5 to about 50 inhalations or "puffs", or from about 10 to about 30 inhalations or "puffs". Each inhalation or "puff" may deliver from about 0.1 mg to about 3 mg of nicotine particles to the lungs of the user or from about 0.2 mg to about 2 mg of nicotine particles to the lungs of the user or about 1 mg of nicotine particles to the lungs of the user.

The nicotine particles may have any useful concentration of nicotine based on the particular formulation employed. The nicotine particles may have at least about 1% wt nicotine up to about 30% wt nicotine, or from about 2% wt to about 25% wt nicotine, or from about 3% wt to about 20% wt nicotine, or from about 4% wt to about 15% wt nicotine, or from about 5% wt to about 13% wt nicotine. Preferably, about 50 to about 150 micrograms of nicotine may be delivered to the lungs of the user with each inhalation or "puff".

The capsule may hold or contain at least about 5 mg of nicotine particles or at least about 10 mg of nicotine particles. The capsule may hold or contain less than about 900 mg of nicotine particles, or less than about 300 mg of nicotine particles, or less than 150 mg of nicotine particles. The capsule may hold or contain from about 5 mg to about 300 mg of nicotine particles or from about 10 mg to about 200 mg of nicotine particles.

When flavour particles are blended or combined with the nicotine particles within the capsule, the flavour particles may be present in an amount that provides the desired flavour to each inhalation or "puff" delivered to the user.

The nicotine particles may have any useful size distribution for inhalation delivery preferentially into the lungs of a user. The capsule may include particles other than the nicotine particles. The nicotine particles and the other particles may form a powder system.

The capsule may hold or contain at least about 5 mg of a dry powder (also referred to as a powder system) or at least about 10 mg of a dry powder. The capsule may hold or contain less than about 900 mg of a dry powder, or less than about 300 mg of a dry powder, or less than 150 mg of a dry powder. The capsule may hold or contain from about 5 mg to about 300 mg of a dry powder, or from about 10 mg to about 200 mg of a dry powder.

The dry powder or powder system may have at least about 40%, or at least about 60%, or at least about 80%, by weight of the powder system comprised in nicotine particles having a particle size of about 5 micrometers or less, or in a range from about 1 micrometer to about 5 micrometres.

The particles comprising nicotine may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

The particles comprising flavour may have a mass median aerodynamic diameter of about 20 micrometres or greater, or about 50 micrometres or greater, or in a range from about 50 to about 200 micrometres, or from about 50 to about 150 micrometres. The mass median aerodynamic diameter is preferably measured with a cascade impactor.

The dry powder may have a mean diameter of about 60 micrometres or less, or in a range from about 1 micrometres to about 40 micrometres, or in a range from about 1.5 micrometres to about 25 micrometres. The mean diameter refers to the mean diameter per mass and is preferably measured by laser diffraction, laser diffusion or an electronic microscope.

Nicotine in the powder system or nicotine particles may be a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine monopyruvate, nicotine glutamate or nicotine hydrochloride, for example. The compound combining with nicotine to form the salt or salt hydrate may be chosen based on its expected pharmacological effect.

The nicotine particles preferably include an amino acid. Preferably the amino acid may be leucine such as L-leucine. Providing an amino acid such as L-leucine with the particles comprising nicotine, may reduce adhesion forces of the particles comprising nicotine and may reduce attraction between nicotine particles and thus reduce agglomeration of nicotine particles. Similarly, adhesion forces to particles comprising flavour may also be reduced thus agglomeration of nicotine particles with flavour particles is also reduced. The powder system described herein thus may be a free flowing material and possess a stable relative particle size of each powder component even when the nicotine particles and the flavour particles are combined.

Preferably, the nicotine may be a surface modified nicotine salt where the nicotine salt particle comprises a coated or composite particle. A preferred coating or composite material may be L-leucine. One particularly useful nicotine particle may be nicotine bitartrate with L-leucine.

The powder system may include a population of flavour particles. The flavour particles may have any useful size distribution for inhalation delivery selectively into the mouth or buccal cavity of a user.

The powder system may have at least about 40%, or at least about 60%, or at least about 80%, by weight of the population of flavour particles of the powder system comprised in particles having a particle size of about 20 micrometres or greater. The powder system may have at least about 40% or at least about 60%, or at least about 80%, by weight of the population of flavour particles of the powder system comprised in particles having a particle size of about 50 micrometres or greater. The powder system may have at least about 40% or at least about 60%, or at least about 80%, by weight of the population of flavour particles of the powder system comprised in particles having a particle size in a range from about 50 micrometer to about 150 micrometres.

The particles comprising flavour may include a compound to reduce adhesion forces or surface energy and resulting agglomeration. The flavour particle may be surface modified with an adhesion reducing compound to form a coated flavour particle. One preferred adhesion reducing compound may be magnesium stearate. Providing an adhesion reducing compound such as magnesium stearate with the flavour particle, especially coating the flavour particle, may reduce adhesion forces of the particles comprising flavour and may reduce attraction between flavour particles and thus reduce agglomeration of flavour particles. Thus agglomeration of flavour particles with nicotine particles may also be reduced. The powder system described herein thus may possess a stable relative particle size of the particles comprising nicotine and the particles comprising flavour even when the nicotine particles and the flavour particles are combined. The powder system preferably may be free flowing.

Conventional formulations for dry powder inhalation contain carrier particles that serve to increase the fluidization of the active particles since the active particles may be too small to be influenced by simple airflow though the inhaler. The powder system may comprise carrier particles. These carrier particles may be a saccharide such as lactose or mannitol that may have a particle size greater than about 50 micrometres. The carrier particles may be utilized to improve dose uniformity by acting as a diluent or bulking agent in a formulation.

The powder system utilized with the nicotine powder delivery system described herein may be carrier-free or substantially free of a saccharide such as lactose or mannitol. Being carrier-free or substantially free of a saccharide such as lactose or mannitol may allow the nicotine and to be inhaled and delivered to the user's lungs at inhalation or airflow rates that are similar to typical smoking regime inhalation or airflow rates.

The nicotine particles and a flavour may be combined in a single capsule. As described above, the nicotine particles and a flavour may each have reduced adhesion forces that result in a stable particle formulation where the particle size of each component does not substantially change when combined. Alternatively, the powder system includes nicotine particles contained within a single capsule and the flavour particles contained within a second capsule.

The nicotine particles and flavour particles may be combined in any useful relative amount so that the flavour particles are detected by the user when consumed with the nicotine particles. Preferably the nicotine particles and a flavour particles form at least about 90% wt or at least about 95% wt or at least about 99% wt or 100% wt of the total weight of the powder system.

The inhaler and inhaler system may be less complex and have a simplified airflow path as compared to conventional dry powder inhalers. Advantageously, rotation of the capsule within the inhaler body aerosolizes the nicotine particles or powder system and may assist in maintaining a free flowing powder. Thus, the inhaler article may not require the elevated inhalation rates typically utilized by conventional inhalers to deliver the nicotine particles described above deep into the lungs.

The inhaler article may use a flow rate of less than about 5 L/min or less than about 3 L/min or less than about 2 L/min or about 1.6 L/min. Preferably, the flow rate may be in a range from about 1 L/min to about 3 L/min or from about 1.5 L/min to about 2.5 L/min. Preferably, the inhalation rate or flow rate may be similar to that of Health Canada smoking regime, that is, about 1.6 L/min.

The inhaler system may be used by a consumer like smoking a conventional cigarette or vaping an electronic cigarette. Such smoking or vaping may be characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

All scientific and technical terms used herein have meanings commonly used in the art unless otherwise specified. The definitions provided herein are to facilitate understanding of certain terms used frequently herein.

The terms "upstream" and "downstream" refer to relative positions of elements of the inhaler described in relation to the direction of inhalation air flow as it is drawn through the body of the inhaler from a distal end portion to the mouthpiece portion.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

FIG. 1 is an exploded perspective view of an illustrative inhaler system.

FIG. 2 is a transparent perspective view of an illustrative inhaler system.

FIG. 3 is a cross-sectional schematic diagram of an illustrative piercing device.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

An inhaler system 100 includes an inhaler article 110 and a piercing device 150. The inhaler article 110 comprises a body 112 defining an inhaler outer surface. The body 112 extends along an inhaler longitudinal axis from mouthpiece end 116 to a distal end 118 a body length.

The piercing device 150 includes a housing 151, defining an outer surface and a housing inner surface 152. The housing inner surface 152 defines an inhaler article cavity 157. The housing 151 extends along a housing longitudinal axis from a distal end 155 to an open proximal end 153 a housing length. The housing open proximal end 153 is configured to receive the distal end 118 of the inhaler article 110 into the inhaler article cavity 157.

A piercing element 160 is contained within and fixed to the housing 151 or distal end 155. The piercing element 160 extends along a piercing element longitudinal axis from a fixed distal end 161 to a piercing end 162 a piercing element length. The piercing element 160 is recessed from the open proximal end 153 a recessed distance.

A marking element 170 extends into the inhaler article cavity 157 from the housing inner surface 152. The marking element 170 is configured to mark the inhaler outer surface 112 when received within the inhaler article cavity 157.

Figure 2:
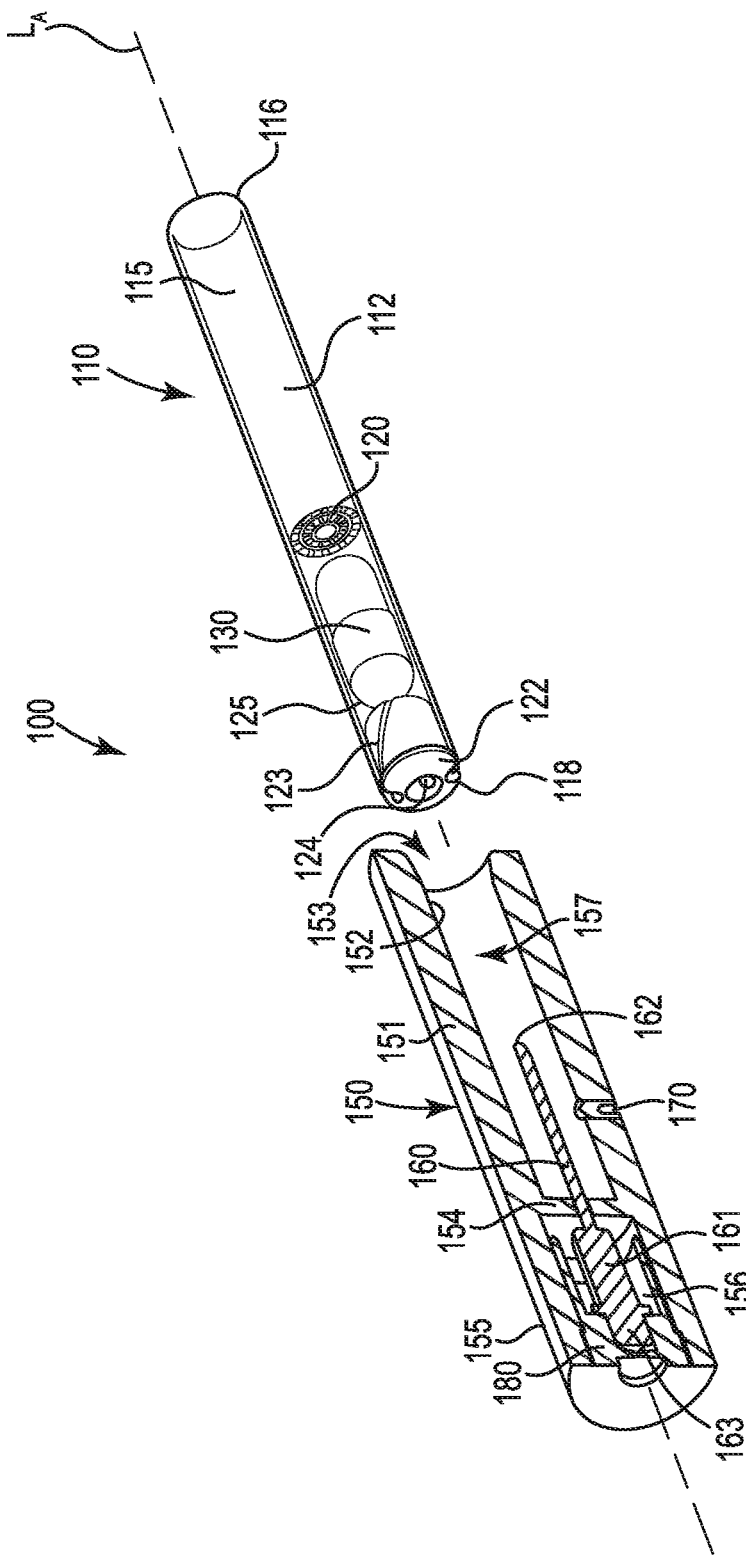

FIG. 1 illustrates an exploded perspective view an exemplary inhaler system 100. FIG. 2 is a transparent perspective view of an illustrative inhaler system 100. The inhaler system 100 includes an inhaler article 110 and a separate piercing device 150. The inhaler article 110 may be received within the piercing device 150 to activate or pierce a capsule 130 disposed within the inhaler article 110. The inhaler article 110 is withdrawn from the piercing device 150 prior to use by the consumer.

The inhaler article 110 includes a body 112 extending along a longitudinal axis $L_A$ from a mouthpiece end 116 to a distal end 118 and a capsule cavity 125 defined within the body 112. The body 112 may have a uniform diameter of about 7.5 mm and a length of about 55 mm. The body 112 may have a uniform diameter inner diameter of about 6.5 mm. The body 112 may have a uniform thickness about 1 mm. A mouthpiece air channel 115 extends from the capsule cavity 125 to the mouthpiece end 116. An end cap or end element 122 is disposed within the distal end 118 and extends to the capsule cavity 125. The end cap or end element 122 includes an air channel 123 extending along the end cap or end element 122. The air channel 123 creates a swirling airflow through the capsule cavity 125. The end cap or end element 122 and a boundary element 120 bound the capsule cavity 125. A capsule 130 is disposed within the capsule cavity 125. The capsule 130 contains particles comprising nicotine. The end cap or end element 122 and the boundary element 120 cooperate to contain the capsule 130 longitudinally within the capsule cavity 125. The capsule 130 axis of rotation may be coextensive with the longitudinal axis $L_A$.

The inhaler article end cap or end element 122 may include a linear piercing channel 124 extending through the length of the end cap or end element 122. The linear piercing channel 124 may be co-axial with the longitudinal axis $L_A$ of the inhaler body 112. The linear piercing channel 124 may be sized to allow a piercing element 160 to pass through the linear piercing channel 124. The end cap or end element 122 may define a resealable element disposed along or within the linear piercing channel 124. Resealable elements or membranes may include a septum or septum-like element. Resealable elements or membranes may be formed of elastic material such as rubber, silicone, metal foil co-laminated with a polymer, or latex and the like, or cellulose acetate tow, such as high-density cellulose acetate tow.

Figure 3:
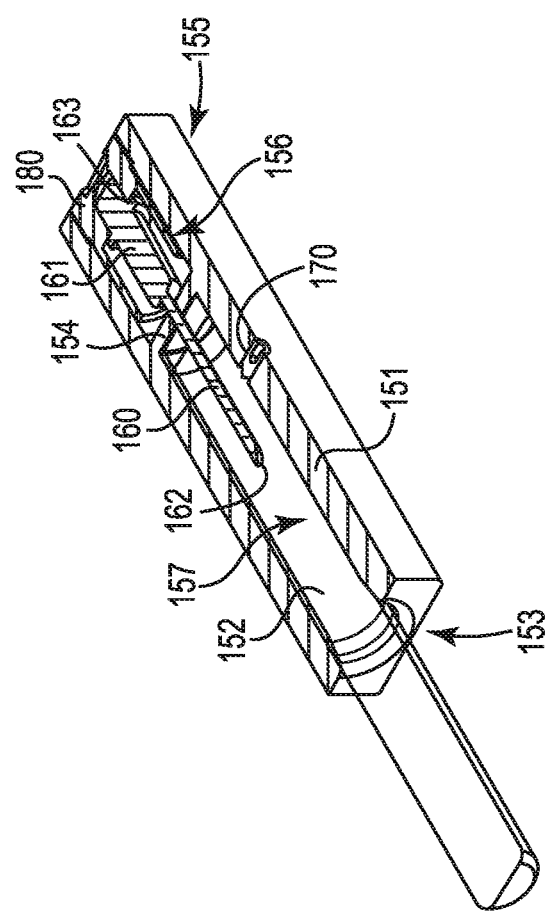

FIG. 3 is a cross-sectional schematic diagram of an illustrative piercing device 150. The piercing device 150 includes a housing 151 defining a housing outer surface and a housing inner surface 152. The housing extends along a housing longitudinal axis $L_A{}'$ (see FIG. 2) from a distal end 155 to an open proximal end 153, a housing length may be about 60 mm. The distal end 155 is illustrated as a closed end cap.

The housing open proximal end 153 is configured to receive the distal end 118 of the inhaler article 110. A piercing element 160 is contained within and fixed to the housing 152 or distal end 151. The piercing element 160 may be removable and replaceable within the inhaler article 150.

The inhaler article cavity 157 may have a closed distal end 154 and the piercing element 160 may extend through the closed distal end 154. The closed distal end 154 may have an aperture sized to receive and allow the piercing element 160 to extend through the aperture.

The closed distal end 154 may define a base of a piercing element cavity 156 defined at the distal end 155 of the housing 151. The piercing element cavity 156 may receive the piercing element 160. The piercing element 160 may include a collar 163 to fix the piercing element 160 within the piercing element cavity 156.

A retaining element 180 may be configured to retain the piercing element 160 within the piercing element cavity 156. The retaining element 180 may form a portion of the distal end 155 of the housing 151 and the retaining element 180 may be removably coupled to the housing 151.

The inhaler system 100 may be utilized by inserting the inhaler article 110 into the piercing device 150 until the piercing element 160 to extend into the capsule 130. The marking element 170 places a mark on the inhaler outer surface 112 to indicate that the capsule 130 has been activated or pierced. Then the inhaler article 110 is withdrawn from the piercing device 150 and consumed by the user. The user may then repeat this method with the piercing device 150 and further non-activated inhaler articles 110.

The invention claimed is:

1. A piercing device comprising:
   a housing, having a housing outer surface and a housing inner surface, the housing inner surface defining an inhaler article cavity, the housing extending along a housing longitudinal axis from a distal end to an open proximal end a housing length, the housing open proximal end is configured to receive the distal end of an inhaler article into the inhaler article cavity;
   a piercing element fixed to and extending from the housing inner surface, into the inhaler article cavity along a piercing element longitudinal axis a piercing element length, the piercing element being recessed from the open proximal end a recessed distance; and
   a marking element extending into the inhaler article cavity from the housing inner surface, the marking element extends orthogonally to the piercing element longitudinal axis, the marking element configured to mark the surface of an inhaler article when the inhaler article is received within the inhaler article cavity.

2. The piercing device according to claim 1, wherein the marking element has a sharp end configured to scratch the outer surface of an inhaler article when the inhaler article is received within the inhaler article cavity.

3. The piercing device according to claim 1, wherein the marking element is configured to apply a color to the outer surface of an inhaler article when the inhaler article is received within the inhaler article cavity.

4. The piercing device according to claim 1, wherein the marking element is configured to mark the outer surface of an inhaler article when the piercing element penetrates a capsule disposed within the inhaler article.

5. The piercing device according to claim 1, wherein the piercing element is recessed from the open proximal end a recessed distance of at least about 25% of the housing length.

6. The piercing device according to claim 1, wherein the piercing element is formed from a metal.

7. The piercing device according to claim 1, wherein the piercing element longitudinal axis is substantially coaxial with the housing longitudinal axis, and an inhaler longitudinal axis, when the inhaler article is received within the piercing device.

8. The piercing device according to claim 1, wherein the piercing element length is about 25% to about 60% of the housing length.

9. The piercing device according to claim 1, wherein the inhaler article cavity has a closed distal end and the piercing element extends through the closed distal end.

10. The piercing device according to claim 9, further comprising a piercing element cavity defined at the distal end of the housing and the closed distal end defines a base of the piercing element cavity and the piercing element cavity receives the piercing element.

11. The piercing device according to claim 10, further comprising a retaining element configured to retain the piercing element within the piercing element cavity.

12. The piercing device according to claim 11, wherein the retaining element forms a portion of the distal end of the housing and the retaining element is removably coupled to the housing.

13. An inhaler system comprising:
an inhaler article comprising a body having an outer surface, the body extending along an inhaler longitudinal axis from a mouthpiece end to a distal end, a body length; and
the piercing device according to claim 1, wherein the piercing device marking element marks the outer surface of the inhaler article when the inhaler article is received in the inhaler article cavity.

14. The inhaler system according to claim 13, further comprising a capsule disposed within the inhaler article, the marking element is configured to mark the outer surface of the inhaler article when the piercing element penetrates the capsule.

* * * * *